US010916339B2

(12) United States Patent
Hanina et al.

(10) Patent No.: US 10,916,339 B2
(45) Date of Patent: *Feb. 9, 2021

(54) MEDICATION ADHERENCE MONITORING SYSTEM AND METHOD

(71) Applicant: AIC Innovations Group, Inc., New York, NY (US)

(72) Inventors: Adam Hanina, New York, NY (US); Gordon Kessler, Mt. Kisco, NY (US); Lei Guan, Harrison, NJ (US)

(73) Assignee: AIC Innovations Group, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/679,808

(22) Filed: Nov. 11, 2019

(65) Prior Publication Data

US 2020/0098459 A1 Mar. 26, 2020

Related U.S. Application Data

(63) Continuation of application No. 15/985,285, filed on May 21, 2018, now Pat. No. 10,475,533, which is a
(Continued)

(51) Int. Cl.
*G16H 20/10* (2018.01)
*G06K 9/00* (2006.01)
(Continued)

(52) U.S. Cl.
CPC ........... *G16H 20/10* (2018.01); *A61B 5/0022* (2013.01); *A61B 5/1128* (2013.01);
(Continued)

(58) Field of Classification Search
CPC .. G06F 19/3456; G06K 9/00771; G06K 9/00; A61B 5/1128; A61B 5/4833; G06Q 50/22; H04N 7/183
See application file for complete search history.

(56) References Cited

U.S. PATENT DOCUMENTS 3,814,845 A 6/1974 Hurlbrink et al.
5,065,447 A 11/1991 Barnsley et al.
(Continued)

FOREIGN PATENT DOCUMENTS

EP 2 968 074 A1 1/2016
WO WO 2011/091413 A1 7/2011

OTHER PUBLICATIONS

Ammouri, et al., Face and Hands Detection and Tracking Applied to the Monitoring of Medication Intake, Computer and Robot Vision, 2008. CRV '08. Canadian Conference, 147(154):28-30, (May 2008).
(Continued)

*Primary Examiner* — Nam D Pham
(74) *Attorney, Agent, or Firm* — Fish & Richardson P.C.

(57) ABSTRACT

A medication management system is described that is operable to determine whether a user is actually following a protocol, provide additional assistance to a user, starting with instructions, video instructions, and the like, and moving up to contact from a medication administrator if it is determined that the user would need such assistance in any medical adherence situation, including clinical trial settings, home care settings, healthcare administration locations, such as nursing homes, clinics, hospitals and the like. Suspicious activity on the part of a patient or other user of the system is identified and can be noted to a healthcare provider or other service provider where appropriate.

15 Claims, 5 Drawing Sheets

Related U.S. Application Data continuation of application No. 15/618,944, filed on Jun. 9, 2017, now Pat. No. 9,977,870, which is a continuation of application No. 14/735,394, filed on Jun. 10, 2015, now Pat. No. 9,679,113.

(60) Provisional application No. 62/010,983, filed on Jun. 11, 2014.

(51) Int. Cl.

| | | |
|---|---|---|
| *G06Q 50/22* | (2018.01) | |
| *A61B 5/11* | (2006.01) | |
| *A61B 5/00* | (2006.01) | |
| *G16H 20/13* | (2018.01) | |
| *H04N 7/18* | (2006.01) | |

(52) U.S. Cl.
CPC .............. *A61B 5/4833* (2013.01); *G06K 9/00* (2013.01); *G06K 9/00771* (2013.01); *G06Q 50/22* (2013.01); *G16H 20/13* (2018.01); *H04N 7/183* (2013.01)

(56) References Cited

U.S. PATENT DOCUMENTS

| | | | |
|---|---|---|---|
| 5,441,047 A | 8/1995 | David et al. | |
| 5,544,649 A | 8/1996 | David et al. | |
| 5,619,991 A | 4/1997 | Sloane | |
| 5,646,912 A | 7/1997 | Cousin | |
| 5,752,621 A | 5/1998 | Passamante | |
| 5,764,296 A | 6/1998 | Shin | |
| 5,810,747 A | 9/1998 | Brundy et al. | |
| 5,911,132 A | 6/1999 | Sloane | |
| 5,961,446 A | 10/1999 | Beller et al. | |
| 6,151,521 A | 11/2000 | Guo et al. | |
| 6,154,558 A | 11/2000 | Hsieh | |
| 6,233,428 B1 | 5/2001 | Fryer | |
| 6,283,761 B1 | 9/2001 | Joao | |
| 6,380,858 B1 | 4/2002 | Yarin et al. | |
| 6,409,661 B1 | 6/2002 | Murphy | |
| 6,421,650 B1 | 7/2002 | Goetz et al. | |
| 6,483,993 B1 | 11/2002 | Misumi et al. | |
| 6,484,144 B2 | 11/2002 | Martin et al. | |
| 6,535,637 B1 | 3/2003 | Wootton et al. | |
| 6,611,206 B2 | 8/2003 | Eshelman et al. | |
| 6,705,991 B2 | 3/2004 | Bardy | |
| 6,879,970 B2 | 4/2005 | Shiffman et al. | |
| 6,988,075 B1 | 1/2006 | Hacker | |
| 7,184,047 B1 | 2/2007 | Crampton | |
| 7,184,075 B2 | 2/2007 | Reiffel | |
| 7,256,708 B2 | 8/2007 | Rosenfeld et al. | |
| 7,277,752 B2 | 10/2007 | Matos | |
| 7,304,228 B2 | 12/2007 | Bryden et al. | |
| 7,307,543 B2 | 12/2007 | Rosenfeld et al. | |
| 7,317,967 B2 | 1/2008 | DiGianfilippo et al. | |
| 7,340,077 B2 | 3/2008 | Gokturk | |
| 7,359,214 B2 | 4/2008 | Heard | |
| 7,395,214 B2 | 7/2008 | Shillingburg | |
| 7,415,447 B2 | 8/2008 | Shiffman et al. | |
| 7,448,544 B1 | 11/2008 | Louie et al. | |
| 7,562,121 B2 | 7/2009 | Berisford et al. | |
| 7,627,142 B2 | 12/2009 | Kurzweil et al. | |
| 7,657,443 B2 | 2/2010 | Crass et al. | |
| 7,692,625 B2 | 4/2010 | Morrison et al. | |
| 7,747,454 B2 | 6/2010 | Bartfeld et al. | |
| 7,761,311 B2 | 7/2010 | Clements et al. | |
| 7,769,465 B2 | 8/2010 | Matos | |
| 7,774,075 B2 | 8/2010 | Lin et al. | |
| 7,874,984 B2 | 1/2011 | Elsayed et al. | |
| 7,881,537 B2 | 2/2011 | Ma et al. | |
| 7,908,155 B2 | 3/2011 | Fuerst et al. | |
| 7,912,733 B2 | 3/2011 | Clements et al. | |
| 7,956,727 B2 | 6/2011 | Loncar | |
| 7,983,933 B2 | 7/2011 | Karkanias et al. | |
| 8,321,284 B2 | 11/2012 | Clements et al. | |
| 8,538,775 B2 | 9/2013 | Skomra | |
| 2001/0049673 A1 | 12/2001 | Dulong et al. | |
| 2001/0056358 A1 | 12/2001 | Dulong et al. | |
| 2002/0026330 A1 | 2/2002 | Klein | |
| 2002/0093429 A1 | 7/2002 | Matsushita et al. | |
| 2002/0143563 A1 | 10/2002 | Hufford et al. | |
| 2003/0164172 A1 | 9/2003 | Chumas et al. | |
| 2003/0190076 A1 | 10/2003 | Delean | |
| 2003/0194374 A1 | 10/2003 | Heasley et al. | |
| 2003/0225325 A1 | 12/2003 | Kagermeier et al. | |
| 2004/0100572 A1 | 5/2004 | Kim | |
| 2004/0107116 A1 | 6/2004 | Brown | |
| 2004/0155780 A1 | 8/2004 | Rapchak | |
| 2005/0144150 A1 | 6/2005 | Ramamurthy et al. | |
| 2005/0149361 A1 | 7/2005 | Saus et al. | |
| 2005/0180610 A1 | 8/2005 | Kato et al. | |
| 2005/0182664 A1 | 8/2005 | Abraham-Fuchs et al. | |
| 2005/0234381 A1 | 10/2005 | Niemetz et al. | |
| 2005/0267356 A1 | 12/2005 | Ramasubramanian et al. | |
| 2006/0066584 A1 | 3/2006 | Barkan | |
| 2006/0218011 A1 | 9/2006 | Walker et al. | |
| 2006/0238549 A1 | 10/2006 | Marks | |
| 2007/0008112 A1 | 1/2007 | Covannon et al. | |
| 2007/0008113 A1 | 1/2007 | Spoonhower et al. | |
| 2007/0030363 A1 | 2/2007 | Cheatle et al. | |
| 2007/0118389 A1 | 5/2007 | Shipon | |
| 2007/0194034 A1 | 8/2007 | Vasiadis | |
| 2007/0233035 A1 | 10/2007 | Wehba et al. | |
| 2007/0233049 A1 | 10/2007 | Wehba et al. | |
| 2007/0233050 A1 | 10/2007 | Wehba et al. | |
| 2007/0233281 A1 | 10/2007 | Wehba et al. | |
| 2007/0233520 A1 | 10/2007 | Wehba et al. | |
| 2007/0233521 A1 | 10/2007 | Wehba et al. | |
| 2007/0265880 A1 | 11/2007 | Bartfeld et al. | |
| 2007/0273504 A1 | 11/2007 | Tran | |
| 2008/0000979 A1 | 1/2008 | Poisner | |
| 2008/0093447 A1 | 4/2008 | Johnson et al. | |
| 2008/0114226 A1 | 5/2008 | Music et al. | |
| 2008/0114490 A1 | 5/2008 | Jean-Pierre | |
| 2008/0138604 A1 | 6/2008 | Kenney et al. | |
| 2008/0140444 A1 | 6/2008 | Karkanias et al. | |
| 2008/0162192 A1 | 7/2008 | Vonk et al. | |
| 2008/0178126 A1 | 7/2008 | Beeck et al. | |
| 2008/0201174 A1 | 8/2008 | Ramasubramanian et al. | |
| 2008/0219493 A1 | 9/2008 | Tadmor | |
| 2008/0275738 A1 | 11/2008 | Shillingburg | |
| 2008/0290168 A1 | 11/2008 | Sullivan et al. | |
| 2008/0297589 A1 | 12/2008 | Kurtz et al. | |
| 2008/0303638 A1 | 12/2008 | Nguyen et al. | |
| 2009/0012818 A1 | 1/2009 | Rodgers | |
| 2009/0018867 A1 | 1/2009 | Reiner | |
| 2009/0043610 A1 | 2/2009 | Nadas et al. | |
| 2009/0048871 A1 | 2/2009 | Skomra | |
| 2009/0095837 A1 | 4/2009 | Lindgren | |
| 2009/0127339 A1 | 5/2009 | Needhan et al. | |
| 2009/0128330 A1 | 5/2009 | Monroe | |
| 2009/0159714 A1 | 6/2009 | Coyne, III et al. | |
| 2009/0217194 A1 | 8/2009 | Martin et al. | |
| 2009/0245655 A1 | 10/2009 | Matsuzaka | |
| 2010/0042430 A1 | 2/2010 | Bartfeld | |
| 2010/0050134 A1 | 2/2010 | Clarkson | |
| 2010/0057646 A1 | 3/2010 | Martin et al. | |
| 2010/0092093 A1 | 4/2010 | Akatsuka et al. | |
| 2010/0136509 A1 | 6/2010 | Mejer et al. | |
| 2010/0138154 A1 | 6/2010 | Kon | |
| 2010/0219097 A1 | 9/2010 | Ramasubramanian et al. | |
| 2010/0255598 A1 | 10/2010 | Melker | |
| 2010/0262436 A1 | 10/2010 | Chen et al. | |
| 2010/0316979 A1 | 12/2010 | Von Bismarck | |
| 2011/0021952 A1 | 1/2011 | Vallone | |
| 2011/0119073 A1 | 5/2011 | Hanina et al. | |
| 2011/0141009 A1 | 6/2011 | Izumi | |
| 2011/0153360 A1 | 6/2011 | Haninia et al. | |
| 2011/0161109 A1 | 6/2011 | Pinsonneault et al. | |
| 2011/0195520 A1 | 8/2011 | Leider et al. | |
| 2011/0275051 A1 | 11/2011 | Hanina et al. | |
| 2012/0075464 A1 | 3/2012 | Derenne et al. | |
| 2012/0086827 A1 | 4/2012 | Hanina et al. | |

(56) References Cited

U.S. PATENT DOCUMENTS

| | | | |
|---|---|---|---|
| 2012/0183941 A1* | 7/2012 | Steinmetz | G06Q 30/02 434/262 |
| 2012/0316897 A1 | 12/2012 | Hanina et al. | |
| 2013/0044196 A1 | 2/2013 | Guan et al. | |
| 2013/0169781 A1 | 7/2013 | Hanina et al. | |

OTHER PUBLICATIONS

Batz, et al. A computer Vision System for Monitoring Medication Intake, in Proc. IEEE 2nd Canadian Conf. on Computer and Robot Vision, Victoria, BC, Canada, pp. 362-369 (2005).
Bilodeau et al. Monitoring of Medication Intake Using a Camera System, Journal of Medical Systems 2011. [retrieved on Feb. 18, 2013] [Retrieved from ProQuest Technology Collection].
Chen, Pauline W., Texting as a Health Tool for Teenagers, The New York Times, Nov. 5, 2009, http://www.nytimes.com/2009/11/05/health/0512/899,510 (3 pages).
Danya International, Inc., Pilot Study Using Cell Phones for Mobile Direct Observation Treatment to Monitor Medication Compliance of TB Patients, Mar. 20, 2009, www.danya.com/MDOT.asp , (2 pages).
EP Communication for EP 3155545, dated Feb. 22, 2018 (6 pages).
EP Supplemental Search Report for EP 3155545, dated Jan. 17, 2018 (3 pages).
Global Tuberculosis Control: A short update to the 2009 report, World Health Organization, (2009) (48 pages).
Huynh et al., Real time detection, tracking and recognition of medication intake, World Academy of Science, Engineering and Technology 60:280-287 (2009).
International Search Report and Written Opinion for App. No. PCT/US15/35240, dated Sep. 14, 2015 (10 pages).
Mintchell, Exploring the Limits of Machine Vision, Automation World, Oct. 1, 2011 (6 pages).
Osterberg, Adherence to Medication, New England Journal of Medicine, 353:487-97, Aug. 4, 2005.
Super-Resolution, Wikipedia, (Oct. 5, 2010) (4 pages).
University of Texas, GuideView, Mar. 15, 2007, http://www.sahs.uth.tmc.edu/MSriram/GuideView, (3 pages).
Valin, et al. Video Surveillance of Medication Intake, Int. Conf. of the IEEE Engineering in Medicine and Biology Society, New York City, USA, Aug. 2006.
Wang et al., Recent Developments in Human Motion Analysis, Pattern Recognition 36(220):585-601 (Nov. 2001).
Whitecup, Morris S., 2008 Patient Adherence Update: New Approaches for Success, www.guideline.com , The Trend Report Series, (Oct. 1, 2008) (17 pages).
EP Communication in European Appln. No. 15806568.0, dated Oct. 20, 2020, 14 pages.

\* cited by examiner

MEDICATION ADHERENCE MONITORING SYSTEM AND METHOD

CROSS REFERENCE TO RELATED APPLICATIONS

This application is a continuation of U.S. patent application Ser. No. 15/985,285, filed May 21, 2018, now U.S. Pat. No. 10,475,533, issued Nov. 12, 2019 to Hanina et al., titled "Medication Adherence Monitoring System and Method", which is a continuation of U.S. patent application Ser. No. 15/618,944, filed Jun. 9, 2017, now U.S. Pat. No. 9,977,870, issued May 22, 2018 to Hanina et al., titled "Medication Adherence Monitoring System and Method", which is a continuation of U.S. patent application Ser. No. 14/735,394, filed Jun. 10, 2015, now U.S. Pat. No. 9,679,113, issued Jun. 13, 2017 to Hanina et al., titled "Medication Adherence Monitoring System and Method", which claims the benefit of U.S. Provisional Patent Application 62/010,983, filed Jun. 11, 2014 to Hanina et al., titled "Medication Adherence Monitoring System and Method," each of which is incorporated herein by reference in its entirety.

This invention was made with government support under grant number 9R44TR000873-02 awarded by National Center for Advancing Translational Sciences, National Institutes of Health. The Government has certain rights in the invention.

FIELD OF THE INVENTION

This invention relates generally to monitoring of patient adherence to a medication administration protocol, and more particularly to a system and method for confirming whether a patient has properly administered their medication according to a predetermined protocol, including advanced analysis and presentation features associated with confirmation of proper medication administration.

BACKGROUND OF THE INVENTION

Dr. Lars Osterberg, M.D. and Dr. Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series*, 2008 *Patient Adherence Update: New Approaches for Success*, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. Further, the inability to confirm a proper prescription regimen being provided to a user in the first place may cause a number of other problems with the use of such medication. As has been shown in regards to various public health medication administration situation, such as administration of tuberculosis medication by the WHO, Directly Observed Treatment (DOT) improves compliance of patients. *Global Tuberculosis Control: A Short Update to the* 2009 *Report*, World Health Organization, 2009. As is shown in this report, funding for implementing DOT programs is high. Thus, the ability to implement such a program with less of a financial burden would be desirable.

Traditionally, participants attend introductions and follow ups for clinical trials in-person. Other patients attempting to adhere to a particular medication protocol similarly are given a prescription and a particular set of instructions from a prescribing medical provider or prescribing doctor, and then compliance is measured at a next visit with that prescribing professional through traditional methods of pill counting, and patient interviews. Thus, data collection is similarly limited to patient visits, rather than on a daily basis. These old methods such as patient questioning and pill counting have been proven to be inadequate measures of adherence and offer no information on dose timing and drug holidays (omission of medication for three or more sequential days).

Compliance technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely unadopted in clinical trials by the pharmaceutical and biotech companies due to their high cost; and d) take a longer time to implement. Further, electronic patient diaries allow for ease of entry of data by a patient. These diaries, however, are still subject to issues related to compliance with medication adherence. Thus, even if a patient is meticulous about entering information into the diary, and thus complying with the requirements for data entry, there is still no guarantee that they are properly taking medication at prescribed times.

Jo Carol et al. stated that "The most reliable method for research purposes, although not practical in a clinical setting, may be a combination approach that includes pill counts, patient self-report, and electronic monitoring." (Carol J. et al, Patterns to Antiretroviral Medication, The Value of Electronic Monitoring, AIDS, 17 (12), pp., 763-767, October 2003). To date, technologies alone have only been used to monitor compliance rather than to encourage it. Furthermore, there has been no comprehensive system provided that allows for the management of multiple patients and multiple patient populations. While current technology may allow poor compliers to be recognized, as will be described below, the proposed apparatus and method of the present invention will help to encourage pharmaceutical compliance and tackle some of the problems that are encountered in the clinical trial process in particular, and the medication protocol monitoring problem in general.

A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of clinical trials and other active patient monitoring of medication adherence.

Most importantly, this system provides no mechanism for actually confirming that a patient is in fact ingesting or otherwise properly administering required medication as required in a clinical drug trial, as prescribed by a prescribing physician in the case where adherence to a particular regimen may prove to be critical to efficacy of the prescription regimen, in various public health scenarios, in situations where failure to keep up a prescription regimen can potentially harm a population as a whole, such as the generation of antibiotic-resistant bacteria strains, in various disease management scenarios, or in home care situations where maintaining proper control of administering healthcare professionals is critical. Further, while the system may be sufficient for one who is in full possession of their mental faculties, any individual who may have difficulty following directions, or one who is actively avoiding medication may still not be taking required medication after it is dispensed. Thus, participants may be forgetful, visually impaired, or otherwise do not believe in the benefit of taking such medication, and may thus not properly log medication administration. Furthermore, the system requires preloading of various medications into a dispenser, and thus likely requires regular visits by an administering manager to be sure appropriate medications are in fact properly loaded therein. It is surely possible that an inexperienced user may place incorrect medications into the device, or may somehow provide incorrect dosages into the device. Additionally, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures. Finally, this system is expensive and requires constant maintenance to confirm that the various mechanical parts are in working order.

U.S. patent application Ser. No. 11/839,723, filed Aug. 16, 2007, titled Mobile Wireless Medication Management System, provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or ingestion of the medication, or the relationship of adherence to the efficacy or safety of the drug over time. When requiring adherence to a predetermined protocol for a clinical trial, this is particularly relevant.

Additionally, existing systems fail to maintain an audit trail for post administration review by a medical official or other clinical trial administrator, and further cannot therefore confirm confirmation of proper medication administration or population management.

Therefore, it would be desirable to provide an apparatus that overcomes the drawbacks of the prior art.

SUMMARY OF THE INVENTION

In U.S. patent application Ser. No. 12/620,686, filed Nov. 18, 2009, titled Method and Apparatus for Verification of Medication Administration Adherence; abandoned, U.S. patent application Ser. No. 13/588,377, filed Jul. 26, 2012, titled Method and Apparatus for Verification of Medication Administration, currently pending, U.S. patent application Ser. No. 12/646,383, filed Dec. 23, 2009, titled Method and Apparatus for Verification of Clinical Trial Adherence, abandoned; U.S. patent application Ser. No. 13/558,380, filed Jul. 26, 2012, titled Method and Apparatus for Verification of Clinical Trial Adherence, now U.S. Pat. No. 8,731,961; U.S. patent application Ser. No. 14/244,036, filed Apr. 3, 2014, titled Method and Apparatus for Verification of Medication Adherence, currently pending; U.S. patent application Ser. No. 12/646,603, filed Dec. 23, 2009, titled Method and Apparatus for Management of Clinical Trials, now U.S. Pat. No. 8,666,781; U.S. patent application Ser. No. 14/153,042, filed Jan. 12, 2014, titled Apparatus and Method for Managing Medication Adherence, currently pending; U.S. patent application Ser. No. 12/728,721, filed Mar. 22, 2010, titled Apparatus and Method for Collection of Protocol Adherence Data, currently pending; U.S. patent application Ser. No. 12/815,037, filed Jun. 14, 2010, titled Apparatus and Method for Recognition of Patient Activities When Obtaining Protocol Adherence Data, currently pending; U.S. patent application Ser. No. 12/899,510, filed Oct. 6, 2010, titled Apparatus and Method for Assisting Monitoring of Medication Adherence, now U.S. Pat. No. 8,605,165; U.S. patent application Ser. No. 14/073,525, filed Nov. 6, 2013, titled Apparatus and Method for Monitoring of Medication Adherence, currently pending; U.S. patent application Ser. No. 13/189,518, filed Jul. 24, 2011, titled Method and Apparatus for Monitoring Medication Adherence, currently pending; U.S. patent application Ser. No. 13/235,387, filed Sep. 18, 2011, titled Apparatus and Method for Recognition of Patient Activities, currently pending; U.S. patent application Ser. No. 13/214,201, filed Aug. 21, 2011, titled Apparatus and Method for Determination of Medication Location, currently pending; U.S. patent application Ser. No. 13/674,209, filed Nov. 12, 2012, titled Method and Apparatus for Identification, currently pending; and U.S. patent application Ser. No. 13/831,555, titled Apparatus and Method for Recognition of Suspicious Activities, currently pending; the contents of these applications being incorporated herein by reference, a proposed system, method and apparatus allows for complete control and verification of adherence to a prescribed medication protocol or machine or apparatus use, whether in a health care provider's care, or when self-administered in a homecare situation by a patient.

These applications present a medication management system that may determine whether a user is actually following a protocol, provide additional assistance to a user, starting with instructions, video instructions, and the like, and moving up to contact from a medication administrator if it is determined that the user would need such assistance in any medical adherence situation, including clinical trial settings, home care settings, healthcare administration locations, such as nursing homes, clinics, hospitals and the like. Further, in accordance with present invention, suspicious activity on the part of a patient or other user of the system can be determined, and can be noted to a healthcare provider or other service provider where appropriate.

In accordance with an embodiment of the present invention, one or more statistical or other calculations related to medication adherence may be performed, the results of such calculations preferably being displayed to a healthcare provider on a dashboard or other display, the results further preferably initiating one or more automated sequences for assisting in encouraging medication adherence.

Still other aspects, features and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

The invention will now be described making reference to the following drawings in which like reference numbers denote like structure or steps. Embodiments of the invention can be implemented on a hardware platform that includes an image capture device. Examples of a hardware platform include a smart phone, a desktop computer, a laptop computer, a tablet device, a wearable device such as a smart watch, or any other suitable electronic device. Examples of an image capture device include a camera or scanner and may employ technologies such as CMOS or CCD image sensors, and may be based, for example, on techniques using lasers, radar, infra-red (IR) radiation, ultra-violet (UV) radiation, time-of-flight (TOF) sensing techniques, depth perception techniques, or any other suitable device, technologies and techniques that can capture and/or store images and/or videos. While applicable to various platforms and image capture devices, embodiments of the present invention are particularly useful in situations where resolution of an image capture device, such as a web cam, is limited and/or where processing power of a hardware platform, such as a mobile device, is limited.

Figure 1:
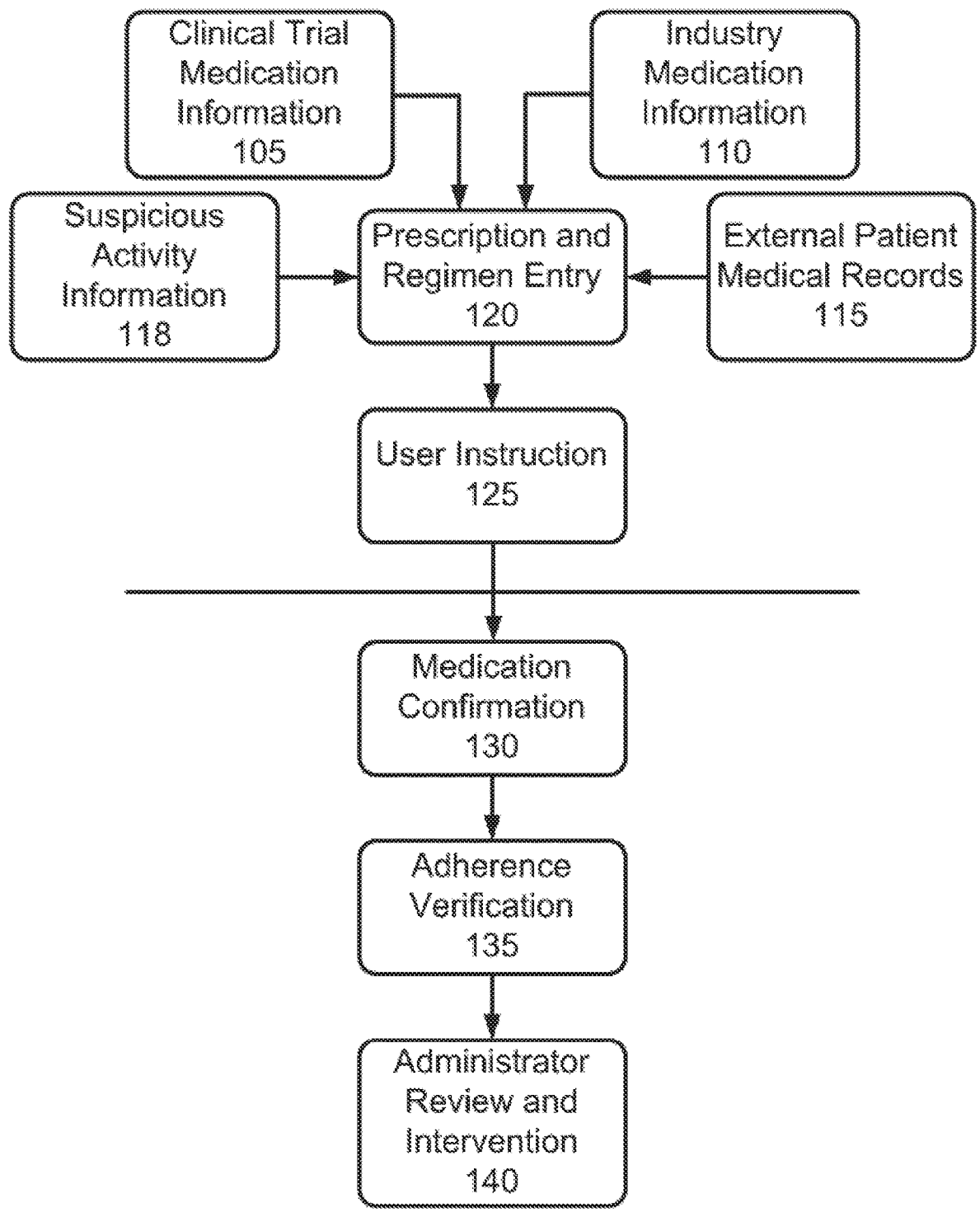
FIG. 1 is a flowchart diagram depicting a method in accordance with an embodiment of the invention.

Referring first to FIG. 1, a data flow overview in accordance with the operation of an embodiment of the present invention is shown. In accordance with this embodiment of the invention, information about a particular drug to be the subject of a clinical trial, to be employed in a public health or disease management situation, or the like, other medication administration program or prescription, or other patient self-administered medical task such as performing a home based urine test or the like may be provided in a database 105, and existing industry medication information databases 110 are preferably employed to access prescription, interaction, application, and other available information about any number of proposed prescription and non-prescription medications and their possible interaction with the clinical trial or other medications. Further, patient medical records 115 may be used, and as will be described below, in conjunction with the industry medical information and a medical professional's prescribing expertise to confirm that a patient is a good candidate for such a clinical trial, or medication administration program. These databases may be accessed in a manner known to one of ordinary skill in the art.

Additionally, one or more predetermined likely typical elements of suspicious or malicious behavior may be provided. Such elements may be based upon the type of medication, method of medication administration, demographics or other information about the patient, other features, or a combination of these elements. Such suspicious activities may further be determined based upon patient profiling of patients, historical determination of likely suspicious activities, prior activity of the particular patient or similarly-situated patients, and the like. Other population based metrics may also be employed, including but not limited to sporadic administration times, suspicious administration times, too short times on task, inconsistent times on task, and any other metric measured from a population found to correlate with predictive suspicious behavior on the part of the participant or patient. Measurement of whether the patient has any medication in their blood, and to the extent no such medication is determined to be in the blood of the patient, the determined suspicious activities may be confirmed to correlate with lack of medication. This correlation may be determined in accordance with various artificial intelligence features, or with one or more supervised, unsupervised, or deep learning techniques. This determined correlation may then be used in the future to infer that the existence of these suspicious activities is predictive of failure to take medication. Suspicious activity information 118 is therefore preferably transferred to the system at this time as well, and as noted above may include one or more indications of patient movements or other actions that may indicate suspicious behavior on behalf of the patient, a malicious intent to trick the system, or actions of other high risk population. The various embodiments of the present invention may also be provided to determine if a patient is performing an action or task correctly or if they are simply making a mistake.

Once confirmed, a medication administration and ingestion or other medication regimen in accordance with the clinical trial or other prescription requirements such as in a public health, medical practice environment or the like may be prescribed and entered into the system of the invention at 120. Such medication administration regimen may include one or more of ingesting or swallowing a pill, using an inhaler device, using an injectable medication device, employing a patch, sublingual administration, a cheek or other skin located medication administration device or the like. The prescription regimen may also comprise one or more pre-administration steps, such as monitoring a medical apparatus, such as a heart rate monitor, blood pressure monitor, glucose monitor, or any other monitor or system that provides an output that potentially effects a medication administration process.

Once entered into the system, a particular prescription regimen may cause a set of user instructions, various training sequences and the like 125 to be generated and transmitted to an apparatus provided to a patient in accordance with an embodiment of the invention for access to the system of the invention. Such an apparatus may comprise a custom designed video and audio capture, analysis and transmission apparatus, a smart phone or other mobile device including an image capture device such as a camera or other video and audio capture apparatuses, a netbook, laptop computer, desktop computer, tablet device or the like, free standing, or built into a mirror or cabinet or the like, or other computing appliance allowing for the display of instructions to a patient, and allowing for the eventual capture, analysis and transmission of video, audio and other analysis information. Additional devices, including one or more wearable sensors, such as a watch with a camera or other sensor, Google Glass®, or other monitoring device may be employed. When installing software on a user's own hardware system, it is preferred that the software detect and otherwise test or determine that the hardware attempting to be utilized by the patient is sufficient to implement the invention and is sufficient to run a software package provided in accordance with the invention. Thus, the software may check that an image capture device such as a camera includes sufficient resolution, that a memory of the device is of sufficient size to allow for sufficient captured video storage, that audio may be properly captured, and that the transmission system includes sufficient bandwidth to transmit and receive captured video, audio, video instructions and the like. Processing may also be performed at a remote location, thus allowing the user to include a lighter application or the like on their local device. Alternatively, the user may employ the local device as a gateway only, all data being transmitted to a remote location for processing, and returning responses as a result of such processing. Thus, a user may be able to dial up a video conference number, or otherwise interact with a remote site, such as by visiting a particular website or URL.

In various alternative embodiments, one or more of the steps noted above may be excluded. For example, a predefined set of user instructions may be provided to all users, such as in a clinical trial or the like. Thus, rather than customizing the user instructions for each individual user, such instructions may be provided for a particular predetermined segment of the population, based upon demographics or other factors, or a single set of instructions may be provided for all users prescribed a particular medication or sequence of medications.

The noted user instructions and training sequences may include general instructions about the particular medication subject to the current trial or medication administration protocol, methods for administration, warnings about side effects, and concerns about drug interactions with common substances or medications, or other medications prescribed to the patient by the system or by another medical service provider. It is contemplated in accordance with an embodiment of the invention that such set of user instructions may be interactive, allowing a user to view additional information about such instructions or prescriptions as desired. These instructions may comprise written, audio or video instructions provided to the user on a display or other information presentation device of the user apparatus. The instructions for a particular user may also be adherence dependent, i.e. if a user has been non-adherent, content describing the importance of good medication adherence, and possibly asking the user for reasons for the adherence may be presented as part of the instructions. Thus, the user may be provided with content at the time of medication administration related to their historical success with medication administration.

It is further contemplated that such instructions may indicate one or more movement sequences to be associated with a corresponding one or more medication administration sequences. These instructions preferably indicate proper and improper motions that may be taken by a patient for ingesting a pill, using an inhaler, using an injectable medication, and the like, and may indicate various motions that may or may not be performed by a user. In such a manner, the patient may be instructed to properly perform all requested actions, and avoid actions that may be indicative of a patient trying to trick the system. The system may be employed in an augmented reality scenario, allowing for active following of medication administration, providing an event for complete, nearly continuous feedback loop.

In an alternative embodiment, it may be possible to particularly not describe to the patient the various suspicious behaviors that will be tracked in an attempt to "trap" the unsuspecting malicious patient. These traps may be maintained and running in a background of the system. Thus, as will be described below, detection of one or more errors may generate real time displayed video and/or audio feedback to the patient in order to correct actions, while one or more other errors may be logged by the system but preferably provide no feedback to the patient, and thus may be accumulated and used to analyze patient actions without providing instructions and help to avoid being caught by the system. After being "caught" a number of times, a state of the user may be changed to one of heightened security awareness. Thus, a user may be first started in a low level of observation. After a predetermined number of potentially actions that are caught, the user may be labeled as a user that is attempting to trick the system, or that is performing one or more suspicious acts, thus warranting a heightened level of security. Additional suspicion will surround review of all actions of the patient. After properly using the system correctly for another predetermined period of time, the user may be returned to the initial normal state. If on the other hand, suspicious activity continues, the user may be moved to yet another state where the user may be recommended to be removed from a clinical trial, or taken off a particular medication, for example.

Such suspicious activity determination may further be performed based upon information retrieved from a plurality of patients in the same clinical trial, taking the same medication, or from a population at large. Any of these group may be further segmented, for example, by demographics and/or adherence levels, in order to aid in determining an appropriate level of surveillance and feedback to be provided to the group. As noted above, this feedback may be provided in the case that the user improperly administers their medication. The user can then be prompted to properly administer their medication by following the subsequent further instructions. The system may then preferably confirm that the user has properly taken their medication by following the further instructions.

In accordance with one or more embodiments of the present invention, one or more of these sets of motions or actions may comprise confirmation that a user has placed a pill in their mouth and has swallowed the pill correctly and has therefore ingested the medication properly through visual confirmation of location, confirmation that the user has properly used an inhaler device through visual confirmation of position and/or audio confirmation of actuation, confirmation that the user has properly used an injectable device through visual confirmation of position and/or audio confirmation of actuation, or the like. Various micro-movements may also be tracked and determined in accordance with the invention. Such micro-movements may include, for example, one or more of swallowing, hand gesture, and/or facial expressions. Faking or miming may be further determined through analysis of these micro movements. A determination of improper medication administration may generate warnings, and further instructions to aid in encouraging the user to properly administer the medication, as noted above. A deep learning, or other supervised or unsupervised learning process may be employed in order to aid in training the system, or in order to improve recognition techniques. In general, deep learning refers to a subfield of machine learning that focuses on learning multiple levels of feature representations in order to model complex relationships among data such as images, sound, and text. Deep learning provides methods for supervised or unsupervised learning of feature representations at successively higher, more abstract levels. Embodiments of the current invention may employ deep learning to help the system to learn complex actions of interest such as micro-movements in conjunction with other motions or actions of a user in order to monitor and detect improper motions.

Figure 2:
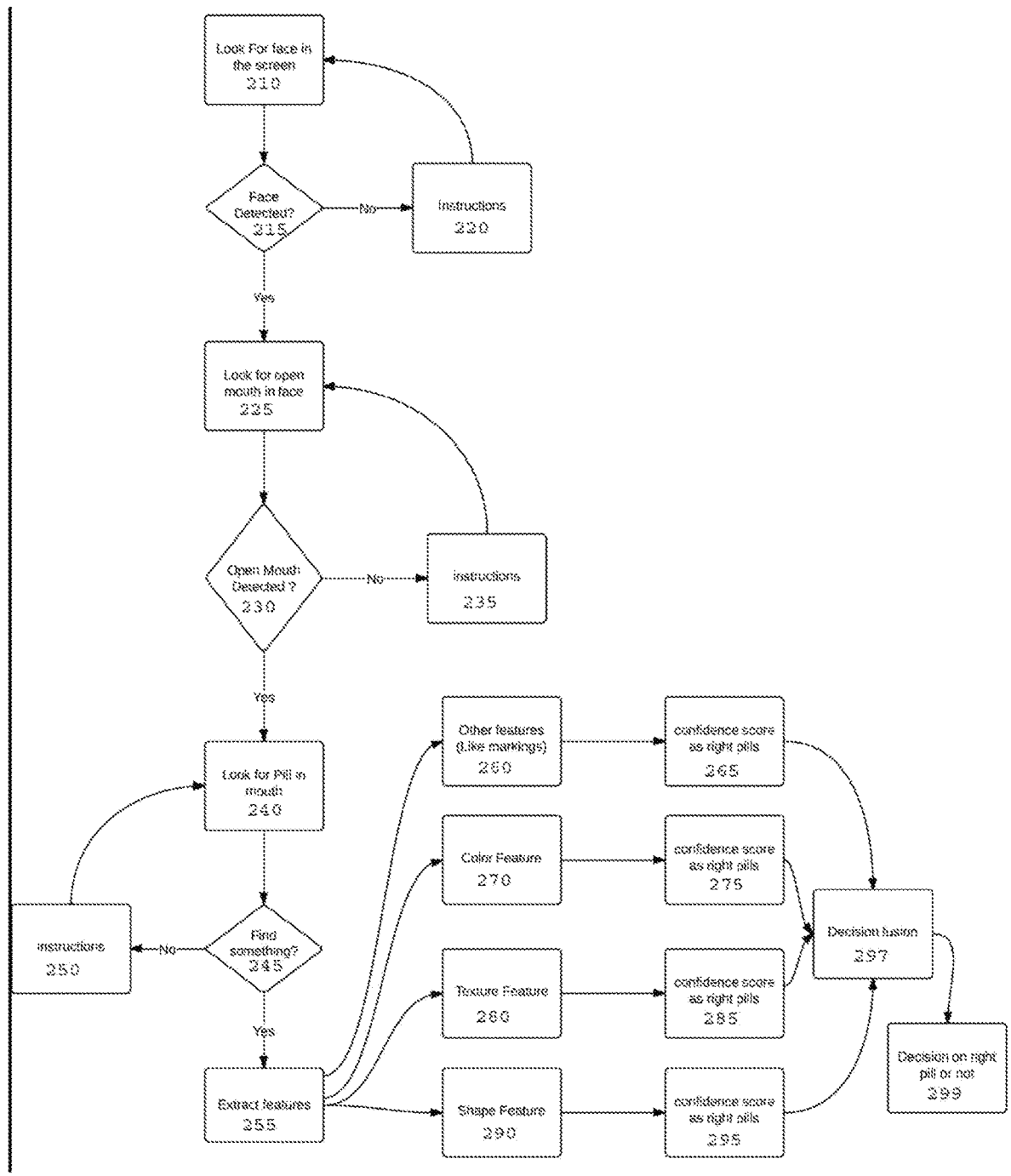
FIG. 2 is a flowchart diagram depicting a method for determining whether a user has taken a pill in accordance with an embodiment of the invention.

Referring next to FIG. 2, a more detailed description of determining whether a user has properly put a pill in their mouth employing a decision fusion process is shown. As is shown in FIG. 2, once an image or plurality of images of the user taking a pill are captured by a mobile device or other image capture device, at step 210 the images are scanned to confirm that the face of a user is in the images. At step 215 it is queried whether the user's face is in the images. If this inquiry is answered in the negative, and it is confirmed that the user's face is not in the images, then at step 220 further instructions are provided to the user to aid them in properly performing the step of properly placing their face in the image, while processing returns to step 210 to acquire a further image or plurality of images.

If the inquiry at step 215 is answered in the affirmative and it is therefore confirmed that the user's face is present and viewable in the images, then processing passes to step 225, where an open mouth of the user is looked for in a further image or plurality of images. Thus at step 230 it is inquired whether the open mouth of the user is able to be detected in the image or images acquired at step 225. If this inquiry is answered in the negative, and it is confirmed that the user's open mouth cannot be detected in the images, then at step 235 further instructions are provided to the user to aid them in properly performing the step of properly showing their open mouth in the images, while processing returns to step 225 to acquire a further image or plurality of images.

If the inquiry at step 230 is answered in the affirmative and it is therefore confirmed that the user's face is present and viewable in the images, then processing passes to step 240 where an image or plurality of images are acquired to determine whether there is a pill in the mouth of the user. Thus, at step 245 it is inquired whether the pill is found in the mouth of the user. If this inquiry is answered in the negative, and it is therefore determined that there is not a pill (or anything else) in the mouth of the user, then processing passes to step 250 where further instructions are provide to the user to aid in properly place the pill in their mouth and properly place their face and mouth in the display to allow for proper confirmation that the pill is present in their mouth.

If the inquiry at step 245 is answered in the affirmative, and it is therefore confirmed that there is a pill or something else in the mouth of the user, processing then passes to step 255 where a feature extraction process is preferably undertaken. In a preferred embodiment, up to four or more features may be extracted, the more features employed, the greater the potential accuracy of the system. Therefore, at step 260, other features, such as marking or other distinctive features may be extracted. At step 270, one or more color features may be extracted, at step 280 one or more texture features may be extracted, and at step 290 one or more shape features may be extracted. At corresponding steps 265, 275, 285 and 295, one or more confidence scores may be determined in accordance with the various feature extractions. Then at step 297, preferably a decision fusion algorithm employing one or more of the determined confidence scores is employed to result in an output at step 299 to confirm whether the pill placed in the mouth of the user is the correct and expected pill. This process may also be employed to identify a pill within the mouth of the user if the features extracted are then compared to a library of features in steps 265, 275, 285 and 295, thus allowing for a selection of a best match from a library of pills, other objects, or the other medications as the case may be. Alternatively or additionally, the system may check the packaging in which the pill is provided to further confirm that the user is administering the proper medication. The system would therefore read text, barcodes, or other indicia on the packaging to recognize and confirm the identity of the medication. Upon removal, the pill may be tracked through the various screens, and the gesture of the hand or other body part of the user may be tracked to further ensure that the medication is removed from the packaging and then properly administered by the user without the possibility of the user not properly administering the medication.

Figure 3:
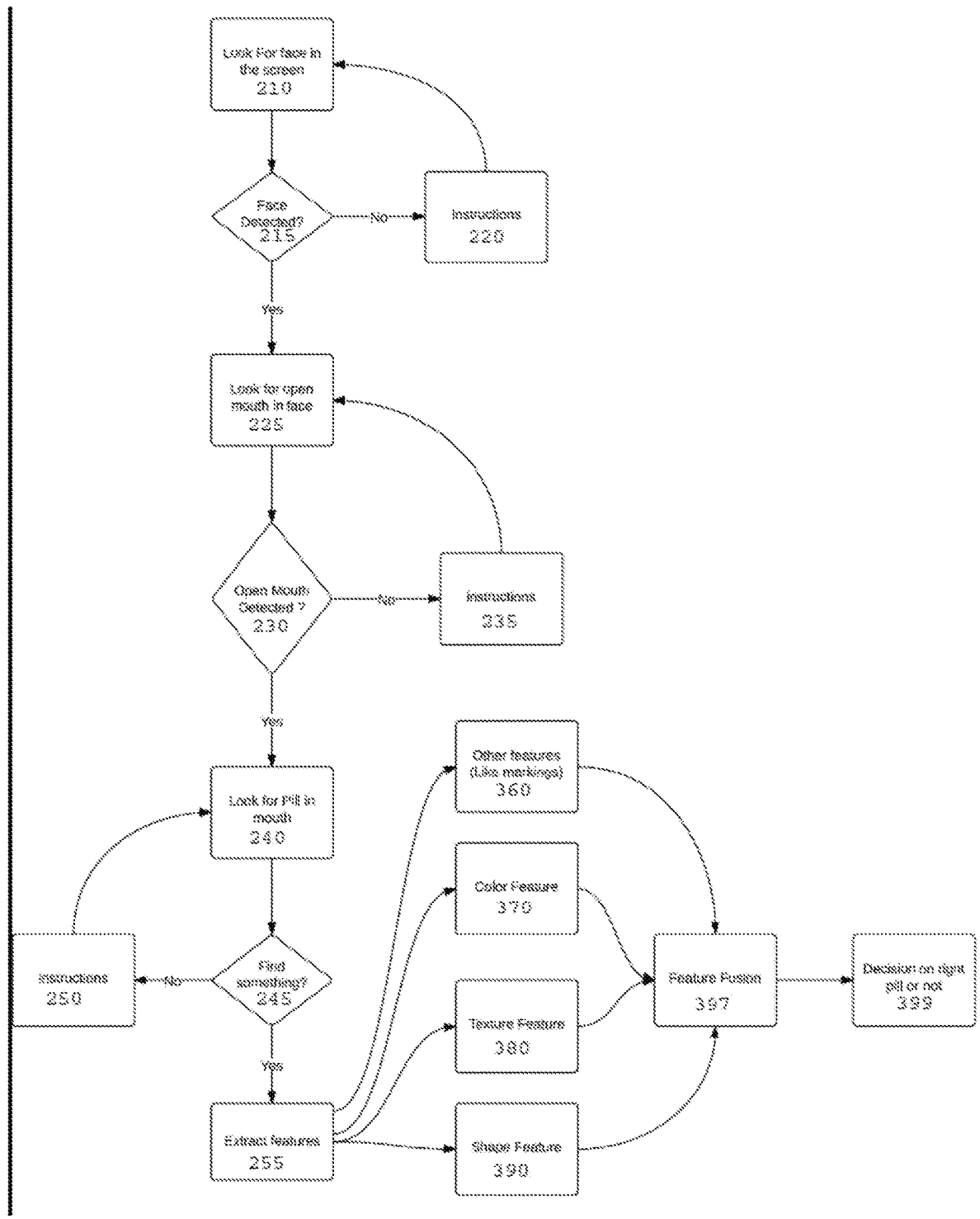
FIG. 3 is a flowchart diagram depicting an additional method for determining whether a user has taken a pill in accordance with an embodiment of the invention.

Referring next to FIG. 3, a further embodiment of the invention for determining whether a user has placed a pill in their mouth employing feature fusion process is shown. The steps 210-255 are similar to those shown in FIG. 2, and will therefore not be described herein. After features are extracted at step 255, these features are confirmed as other features (such as pill markings and the like) at step 360, color features at step 370, texture features at step 380 and shape features at step 390. Other features may also be employed as appropriate. After all of these features are extracted, they are fed into a feature fusion algorithm at step 397, the output of which determines whether a correct pill or other object is in the mouth of the user at step 399. Similarly to as noted above, this feature fusion process may also be employed to determine the identity of one or more pills or other objects from a group of known pills, or from a library of a large number of pills. Furthermore, if a new pill is determined, it is possible to retain this information to allow for a future recognition of the same pill. Thus the acquired extracted features may be used to train or further refine any recognition data employed for pill recognition.

In accordance with the various recognition steps employed in accordance with the various embodiments of the invention, various requests may be made of the user in order to attempt to improve the recognition process. These requests all aid to improve the ability of the camera to properly view the pill in the mouth of the user, and to improve the imaging environment in which the camera is to work. In accordance with the various embodiments of the invention, detailed modeling of the mouth, tongue, teeth, lips and/or gums may be employed. In such a manner, it is therefore possible to extract any such feature if it interferes with the detection of the pill or other object in the mouth. For example, if the pill is white, it may be preferable to extract the teeth of the user to avoid any confusion with the pill. Similar extractions may be employed with the other portions of the mouth of the user based upon the color or other features of the pill. Such detailed modeling is also beneficial when determining whether the user has placed the pill or other medication in the correct location in their mouth, such as when the user is to take a sublingual medication that must be positioned under to tongue to properly dissolve. Such extraction may also be applied to tongue piercings dental fillings, and any other features that may tend to complicate or confuse the pill or medication recognition process.

As noted, such detailed modeling allows for the determination of location of the pill or other medication in the mouth. Thus, proper placement of the pill is important. Additionally, when scanning the mouth, such detailed modeling may also allow for a determination that the user is hiding the pill in a portion of their mouth to avoid taking the medication. Such recognition may be employed to false an alert (in a manner as will be described below) or may be employed to decrease the confidence of any determined medication administration. Thus, the user may be asked to move their tongue up or down in their mouth to allow for a clear view of the mouth to scan for a pill that is supposed to be swallowed. Failure to move the tongue as requested may be logged as a suspicious activity. By modeling the tongue in this manner, it is possible to make detailed determinations of whether the user is properly moving their tongue, and whether they appear to be attempting to hide a pill in their mouth. Additionally, any type of deformation of the cheek or mouth area may be recognized to aid in determining that the user is trying to disguise a movement or motion. Requests for such movement may be provided at any of the instruction steps in FIGS. 2 and 3, and most preferably at step 250 in FIGS. 2 and 3. Various other portions of the mouth may be examined to determine an intent to trick the system, such as any deformation of the cheek of the user that may be attempting to hide a pill or other object therein. Other locations in the mouth may also reviewed to confirm that the pill is not being hidden.

In addition to directly employing the noted visual algorithms, it is possible to employ a number of other checks to aid in determining that the user is properly taking their medication, or alternatively that the user is attempting to trick the system. Thus, in addition to employing audio to listen for the user to spit out the pill or otherwise track noise indicative of the user trying to trick the system. The user may be asked to speak a predetermined word on sentence to determine whether there is any distortion in the audio. Such a system may be employed by asking the user to say the sentence in a training session, either when in the presence of a healthcare worker, or alone, so that there is a comparison that is possible at the later time. In such a manner, these additional features assist in determining whether a user is attempting to trick the system.

In addition to the direct monitoring of one or more parameters related to the actual ingestion of a medication pill or other object, it is further possible to monitor emotions of the user, any edginess, rapid eye movements, or other actions that may lead to a determination that the user is acting untruthfully, or is trying to trick the system. Other monitored movements on the part of the user may comprise swiping of the user's hand over their mouth when the pill has been placed therein, wiping of the mouth, turning of the user's head relative to the camera in an attempt to shield the mouth, not properly tilting the cup when drinking, and therefore pretending to drink or "drink miming", and the like. These movements may also be tracked and monitored in order to further determine proper medication administration, including placing and keeping the medication pill in the mouth.

Various additional features may preferably be provided in order to allow significant flexibility in the monitoring of confirming medication pills are ingested by a user. Thus the system can be provided to track multiple pills for a single administration, multiple types of medication. Environmental checking to confirm the lighting environment is appropriate for the camera (and providing feedback instructions if there is a parameter that needs to change), as well as flashing the display to provide additional light to support low ambient light may also be provided in order to aid in the functionality of the system.

As noted above, various attributes, such as video and/or audio data indicative of different levels of, for example, stress, anxiety, energy, movement, tone of voice, and/or speed of talking, may be employed in order to determine whether the user is performing in a manner that suggests possible attempts to cheat the system. These attributes may further be cross-correlated with known, monitored adherence information and any other questionnaires in order to determine any patterns between measurable behavior and the known adherence profile of the user. Such questionnaires may be presented in visual format, or via an interactive voice recognition system, thus allowing for questions to be presented at the time of poor adherence or the like. Such questions may prompt for information, or an emotional response that may further be correlated to the adherence profile of the user. Responses, or even additional targeted questions may be employed to prompt more favorable behavior patterns from the user. Thus, if particular attributes are determined in the future, it would be possible to increase surveillance, or otherwise attempt to intervene to improve actual adherence, based upon these findings.

In addition, the system may preferably include one or more additional questions that may be provided to the user if any such increased surveillance is necessary, thus trying to ascertain one or more reasons for the poor adherence behavior. Simple or complex questions can be asked, the responses being provided into a system that further is able to predict user behavior. Various emotional responses may be elicited, thus allowing for the determination of whether the user is likely to take their medication in the future. By employing such predictive algorithms, the user may be positioned within a predetermined state machine or other system for predicting behavior based upon historical data, thus allowing for necessary intervention and escalation when poor adherence is predicted. In this manner, the users may be contacted before they fail to take their medication. If such a possibility of poor adherence is determined, and thus intervention may be considered helpful, a customized intervention form a healthcare provider may be provided. This interaction may include automated contact, personal contact, education, incentives and other methods or features to encouraging proper medication adherence. Success or failure of each of these intervention methods may further be tracked and provided as feedback information, thus further allowing for customization and fine tuning of the intervention strategies in the future.

Additional details regarding the modeling and monitoring of positions and movements of the mouth and tongue of the user as well as other micro movements, micro bulges, and micro expressions of the user may also be employed. For example, various machine learning techniques may be employed in order to map and track the position of the tongue. These machine learning techniques may include one or more supervised or unsupervised learning techniques, such as deep learning techniques. In addition to modeling the mouth and tongue of the user, these additional learning techniques may be employed for feature recognition at the time of training the system, as well as for data analysis at the time of system use. Various quadrants may be defined in the mouth of the user, and thus positioning of the tongue may be determined with accuracy, and utilized to further determine proper medication adherence, or an intent to try to trick the system.

Referring back to FIG. 1, at step 130, confirmation of medication is preferably performed employing computer vision and identification in a manner consistent with the device noted above. Adherence is similarly verified in accordance with computer vision and activity recognition. Finally, review, either automated and/or manual is performed of the adherence and confirmation information, and intervention is provided to the user. Details of these confirmation and intervention steps will now be provided.

Figure 4:
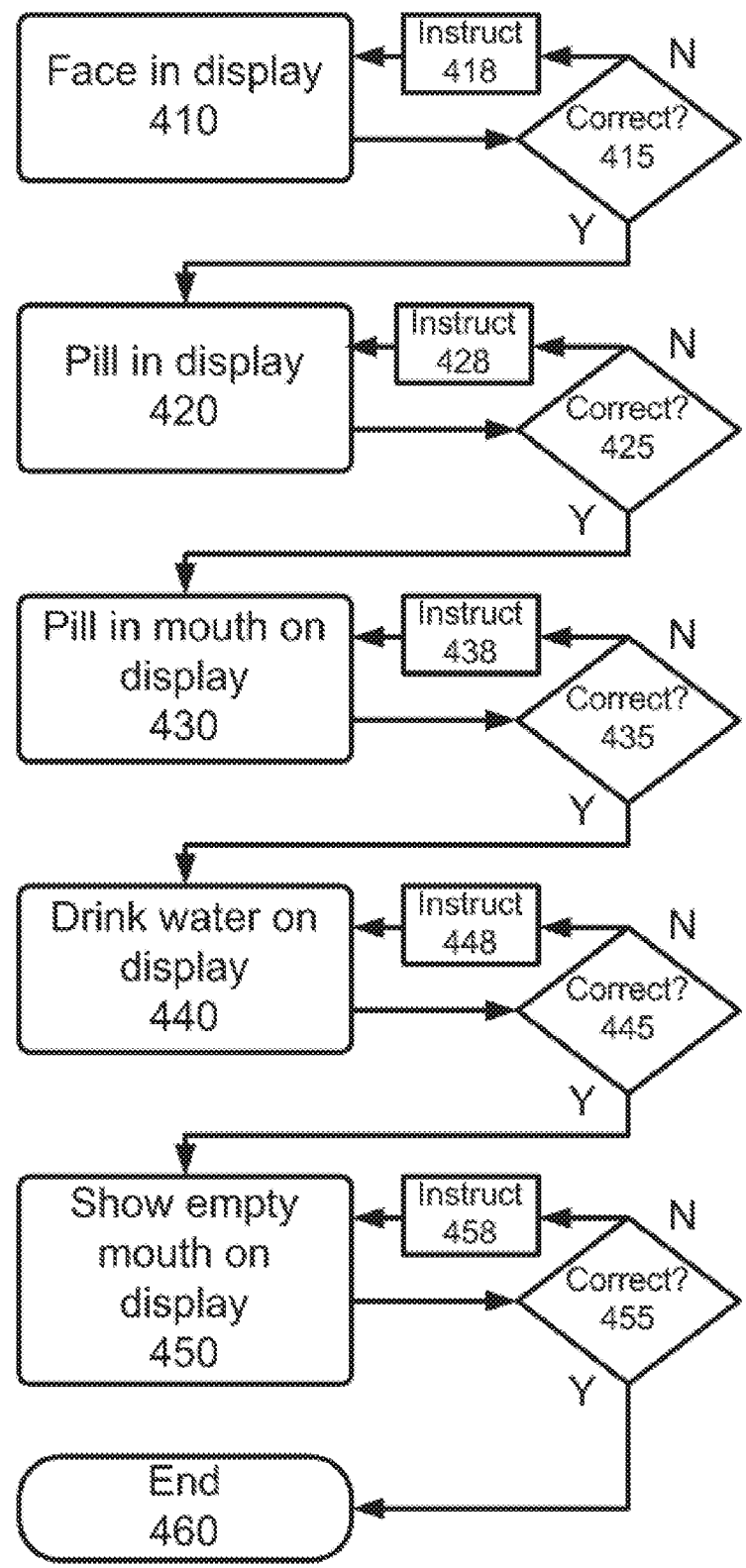
FIG. 4 is a flowchart diagram depicting a process for monitoring medication adherence in accordance with an embodiment of the invention.

Referring next to FIG. 4, a flowchart diagram depicting one possible exemplary flow of processing in accordance with an embodiment of the invention is shown. As shown in FIG. 4, at step 410, a user may be asked to place their face in a display positioned according to one or more instructions, prompts, masks, or the like on the display or a device coupled to, or including a camera for imaging. Processing passes to step 415 where it is determined whether the user has placed their face in the correct location on the display. If this query is answered in the negative, and it is determined that the user has not placed their face in the proper location, one or more further instructions may be provided at step 418 to aid in encouraging the user to properly perform the current step, before moving on to the next step. The loop of steps 410, 415 and 418 may continue until the inquiry at step 415 is answered in the affirmative, and it is therefore determined that the user has properly placed their face in the display.

Processing then passes to step 420, where the user may be asked to place the medication pill (or other medication) in the display positioned according to one or more instructions, prompts, masks, or the like on the display or a device coupled to, or including a camera for imaging. Processing passes to step 425 where it is determined whether the user has placed the pill in the correct location on the display. If this query is answered in the negative, and it is determined that the user has not placed the pill in the proper location, one or more further instructions may be provided at step 428 to aid in encouraging the user to properly perform the current step, before moving on to the next step. The loop of steps 420, 425 and 428 may continue until the inquiry at step 425 is answered in the affirmative, and it is therefore determined that the user has properly placed the pill in the display.

Processing then passes to step 430 where the user may be asked to show the pill or other medication in their mouth and show this position to the camera to be shown in the display positioned according to one or more instructions, prompts, masks, or the like on the display or a device coupled to, or including a camera for imaging. Processing passes to step 435 where it is determined whether the user has placed the pill properly in their mouth and shown the placement properly to the display. If this query is answered in the negative, and it is determined that the user has not properly placed the pill in their mouth and shown this to the camera at the proper location of the display, one or more further instructions may be provided at step 438 to aid in encouraging the user to properly perform the current step, before moving on to the next step. The loop of steps 430, 435 and 438 may continue until the inquiry at step 435 is answered in the affirmative, and it is therefore determined that the user has properly placed the pill in their mouth and shown the pill-in-mouth to the display.

Processing then passes to step 440 where the user may be asked to drink a glass of water or other liquid in the display positioned according to one or more instructions, prompts, masks, or the like on the display or a device coupled to, or including a camera for imaging. If the user is not using a clear cup, the user may be prompted to use a clear cup so that it can be seen if the user spits the pill out of the user's mouth and hides it inside the cup. If the user does not change the cup, an alert may be provided indicating potentially suspicious behavior. Processing passes to step 445 where it is determined whether the user has properly drank the glass of water in the correct location on the display. If this query is answered in the negative, and it is determined that the user has not drank the glass of water, one or more further instructions may be provided at step 448 to aid in encouraging the user to properly perform the current step, before moving on to the next step. The loop of steps 440, 445 and 448 may continue until the inquiry at step 445 is answered in the affirmative, and it is therefore determined that the user has properly drank the glass of water in the display.

Finally, processing passes to step 450 where the user may be asked to show their empty mouth to the camera to be shown in the display positioned according to one or more instructions, prompts, masks, or the like on the display or a device coupled to, or including a camera for imaging. Processing passes to step 455 where it is determined whether the user has properly shown their empty mouth to the display. If this query is answered in the negative, and it is determined that the user has not properly shown their empty mouth at the proper location on the display, or it is determined that their mouth is not empty, one or more further instructions may be provided at step 458 to aid in encouraging the user to properly perform the current step, before moving on to the next step. Alternatively or additionally, the user may be asked to show the glass of water so that it can be confirmed (for example, through the clear side of the glass or from the top of the glass) that the pill had not been spit out of the mouth of the user. The loop of steps 450, 455 and 458 may continue until the inquiry at step 455 is answered in the affirmative, and it is therefore determined that the user has properly shown their empty mouth and/or the glass of water without the pill inside to the display.

In accordance with various alternative embodiments of the invention, any one or more of the steps may be excluded, preferably based upon a desired level of surveillance, but may be based upon any reason. Additionally, while the example is shown with a single medication pill, multiple of the same or different pills may be employed, as may one or more sublingual or other medications.

Therefore, in accordance with one or more embodiments of the invention, the following results, among others, may be achieved.

1. Analyze audio sound to determine if pill still in mouth—After placing the pill in their mouth, swallowing the pill and confirming their mouth is empty, the system may ask the user to speak something. This wording may be prerecorded by the user so that a comparison with current audio may be made. The audio will be recorded and analyzed. If the sound is abnormal, a suspicious flag will be raised on the dashboard for human inspection.

2. Measure the time the user drinks the water—The time on task data of drinking the water may be monitored and be used by the system to determine if the patient is faking drinking the water. If the time on task is too short comparing with other people, or prior steps performed by the same person, this may suggest the user is cheating. Also, the system can check the water level in the cup as a secondary check. To automate the process, the system can ask the user to show the cup with water. The system may detect the cup and water level and saves the time as start time. After drinking water, the system may ask user to show the cup again. And saves the time as end time. The time difference can be used to determine if drinking water is too fast.

3. Sound detection for detecting spitting the pill. Sound will be recorded and analyzed at critical steps. If spitting sound is detected, suspicious flag will be raised.

4. Detect hand to mouth at critical steps—At critical steps, the system will look for hand around mouth regions. If hand is detected at those critical steps, suspicious flag will be raised.

5. Use reflections of the screen to help pill in mouth confirmation or empty mouth confirmation in dark environment. If a room is dark, the system may have a problem seeing what is in the mouth of the user. The system is then able to analyze the brightness of environment. If the brightness level is below a threshold, the system will ask the user to come closer to the screen and open their mouth. In this situation, the face will be missing, leaving the open mouth showing on the majority of the screen. Then the system will detect the open mouth and check what is in the mouth with the help of reflections from the screen. The screen may be flashed or lit around the perimeter to provide adequate lighting to light the scene.

6. Multiscale detection and fusion to check what is in the mouth. This process can help to make sure it is the right pill in the mouth and can be used to check whether it is dented pill, tongue piercing, teeth or the wrong pill. This process has been described above with respect to FIGS. 2 and 3.

7. Determine duplicate enrollment of a user. Through the analysis of images of the face or other biometric marker of the user, it is possible to determine within a larger group of users whether a particular user has been entered into the system twice. Thus, determining whether the user has a very similar second user in the system may be determined, and then provided to a live operator to confirm whether there is a confirmation that the user has entered the system twice. While this final confirmation may be provided via an automated system, the inventors of the current invention have determined that the use of a manual review after proper prompting by the system allows for a second check of the potential duplicate enrollment, encouraging a failsafe process. The automated notification to the manual review may be performed in accordance with a deep learning, supervised, or unsupervised learning and/or analysis process. One or more dashboards may be provided allowing for the review of images or videos of the potentially duplicate enrolled users. Such dashboards, may provide an automated system to provide a review of such images, or may provide a platform by which a manual user may provide such comparisons.

In various additional embodiments of the invention, the system is preferably adapted to recognize one or more different medications, as well as count a plurality of the same or different pills or other medication administrations. In addition to imaging and recognizing the actual medication, it is also contemplated to allow the system to image and recognize one or more medication bottles, labels or other indicator. This recognition may be employed as a secondary check that the medication is correct, may be substituted as the sole check that the medication is correct, or may further be employed as an initial indication of medication, and then the pill or other medication imaging may confirm that the medication pill or the like is consistent with, for example, the bottle or label as well as a prescription, if appropriate. Furthermore, time on task, as well as any other anomalies determined in the medication administration process may be employed to aid in determining any problems with medication administration by the user.

Therefore, in accordance with one or more embodiments of the invention, determining patterns of behavior based on analysis of different movements, time on task, activities, or even micro movements, bulges, or other deformations in, for example the cheek of the user, or in any detected or audio signals is provided. These patterns of behavior all provide a longer term snapshot of the expected actions of the user, and allow for the determination of suspicious or other incorrect behavior over time. Thus rather than simply considering a single action in time, consideration of actions of a user over time is contemplated in accordance with the various embodiments of the invention. This time line of actions gives a very different picture of activity of a user, and allows for the determination of consistency of action over time. These actions may further consider tracking of hand movements of the use, and removal of medications from the packaging, such as a blister pack, bottle or the like. The above mentioned deep learning system, or other supervised or unsupervised learning may be employed to allow for proper training of the system, and/or for recognition and analysis of user actions. While the invention has been described making reference to pill medications, capsules, sublingual medication, or medication administrable by any other route (such as inhalable or injectable medication), may also be monitored in accordance with one or more of the various embodiments of the invention.

It is further contemplated that the system comprise one or more medication reminders indicating to a user when it is time to take their medication. This reminder may be set by a healthcare provider, or by the user. It is contemplated that the reminder be adjustable within a predefined window set in accordance with the medication prescription. Such flexibility may allow the user to set medication reminders to avoid other activities such as work and sleep.

In each of the above-described embodiments, various escalations for when medication is not taken properly may include one or more of an automated contact, personal contact, request for retraining or the like. Such an escalation process may be predefined, and therefore be automated, prompting intervention and input from a healthcare provider when warranted. In such a manner, the system allows a large number of users to be monitored by a relatively small number of healthcare professionals aided by the inventive system. The system further preferably logs interventions, whether automated or personal, in order to determine for a particular user or group of users, which intervention strategy is most effective. Thus, through the application of such an escalation procedure to a number of users, a most effective escalation process can be defined and applied on a go-forward basis, thus allowing for continual tweaking of the system to provide a most effective monitoring and intervention system.

In addition to monitoring administration, the system may further request various feedback from the user, relating to reasons for skipping medication, side effects, or any other information. Such additional information may be employed to further customize the escalation process to improve the ability of the system and healthcare provider to encourage proper medication adherence.

In addition to monitoring medication administration, the system may also receive information from one or more medication monitoring devices, such as, but not limited to, glucose monitors, heart rate monitors and the like. These systems may transfer information to the system via a wireless protocol such Wi-Fi, Bluetooth, or the like, or the system may image a display from one or more of these devices to read the information presented thereon. Other devices, such as activity monitors, such as the Nike® fit band, FITBIT®, Jawbone UP™ wristband and the like may further be employed to correlate user activity and medication adherence. This information may be included as another input into a decision process that determines adherence, and when adherence fails, is able to correlate user activities, side effects, lack of consistency in medication administration and the like to predict participants who may have future adherence problems. These users may then be contacted to ward off the expected future adherence problems. This information may be used to adjust a prescription, either timing, amount, both, or the like. The information may be further used to predict future adherence to the medication protocol.

While the invention has been described relative to a camera on a mobile device, preferably a smart phone, tablet computing device, or the like, other electronic devices including an image capture device for imaging the medication administration process and providing instructions and other feedback to the user may be employed. Thus, a smart watch, or other device including an image capture device such as a camera and feedback mechanism thereon may be employed in accordance with the various embodiments of the invention. Portable and/or wearable computing devices, such a Google Glass® may be employed to allow for imaging and identification of medication, and for tracking various aspects of the medication administration process. Such a device may be employed in conjunction with an image capture device and other mobile device, thus providing significant additional information to the system to aid in predicting adherence behavior.

Information may further be read from any self-administration medical or other devices having a display thereon, thus by visual imaging, or by connectivity through a local network, or through point to point communications. Chips on pills (such as those currently provided by Proteus Digital Health), one or more electronic pill bottle devices confirming the timing of opening of a pill bottle, breathalyzer type devices, such as those provided by Exhale, RFID tags provided in medication packaging, and other adherence monitoring devices may all provide information to the devices and system of the current invention. It is contemplated, in a manner as noted above, that this various information will be provided to allow for tuning of various escalation procedures, thus providing a most effective monitoring and intervention system.

In addition to receiving various information, it is further contemplated in accordance with the various embodiments of the invention that a dashboard is provided to a healthcare provider or other individual who has interest in the adherence monitoring of the user. All adherence and medication administration is preferably accumulated and displayed to the healthcare provider or other individual on a dashboard-type display. Recommended intervention strategies are also provided to the healthcare provider. In a manner as noted above, these customized intervention strategies may be determined in accordance with one or more of historical adherence for the particular user, historical adherence for the demographic group, disease state, or the like. The healthcare provider or other individual may be provided one or more charts, tables or other information displays to allow for assisted review of the accumulated adherence information. As noted above, by allowing direct intervention and contact with a user via such a dashboard, this not only lightens the burden on the healthcare provider, but also allows for results of various interventions to be tracked and optimized.

The system and dashboard may further allow for the healthcare provider or other individual to receive automated alerts when one or more users has a medication adherence event, or requires intervention or follow up. Thus, the healthcare provider or other individual may receive an email or text message when intervention is recommended. A mobile application version may allow the healthcare provider or other individual to interact with the user via their mobile device, thus allowing for logging and monitoring of any such interventions, while allowing for the flexibility of intervention using a mobile or other convenient device.

Therefore, in accordance with one or more embodiments of the invention, a system to allow for a holistic approach to medication adherence is provided. Adherence monitoring is provided using facial recognition, computer vision and activity recognition, in a non-invasive manner. Adherence information for each individual is accumulated and provided, both individually and in an aggregated manner to a healthcare provider or other individual. Targeted and custom interventions are recommended based upon predictive algorithms that aid in determining when a user might be at risk for poor adherence in the future. Interventions through the system are tracked and analyzed to determine which result in the best future corrective behavior of a user. This information is employed in a feedback to improve and optimize intervention and escalation strategies for the individual user, as well as other user similarly situated with at least one attribute. These optimized interventions are therefore designed to be as non-intrusive as possible while eliciting a change in behavior of the user where change is still possible, and before adherence problems may render prescribed medication ineffective.

While the system has been described employing one or more local devices on the part of the user, cloud based systems allowing the user to interact with the system employing an Internet browser or other remote connection program may be employed. Healthcare providers or other individuals may similarly access various information via a cloud based system, or through information pushed to a local device.

Figure 5:
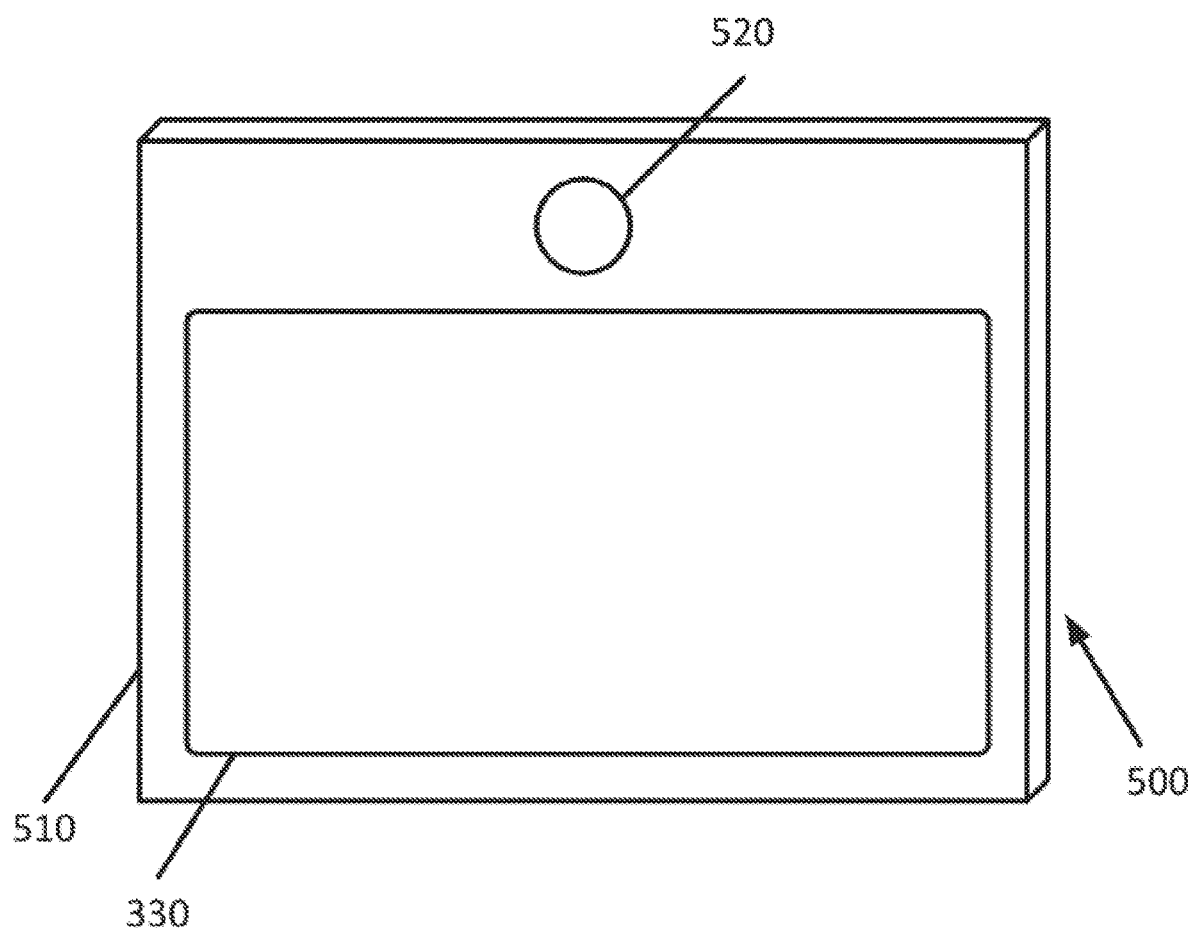
FIG. 5 depicts an exemplary hardware platform for implementation of one or more of the embodiments of the invention.

Additionally, referring to FIG. 5, a display and image capture apparatus 500 that may be employed in accordance with one or more embodiments of the present invention for acquiring one or more images, and for displaying the one or more images and additional material, for performing processing in accordance with the various embodiments of the invention, and for storing computer program instructions, acquired data, and other information on a non-volatile computer readable storage medium is shown. Apparatus 500 preferably includes a housing 510, an image capture device such as an image capture camera 520, and a display or other information presentation device 530 for presenting information visually and/or audibly. Image capture camera 520 may comprise a single camera element, a stereo camera element or other appropriate image capture device. Other elements, as known to one of ordinary skill in the art, including ports, power attachments, processors for processing data, and the like may also be provided in accordance with apparatus 500. It is further contemplated in accordance with the various embodiments of the invention that apparatus may include one or more self-check mechanisms, including mechanisms for determining proper ambient light, direction and background of the camera and the background imaged by the camera, or other environmental issues that may be improved to further aid in the imaging of any images by apparatus 500. Additionally, if at any time it is determined that lighting conditions are too difficult for imaging apparatus 500, it may be possible to provide a light burst from a strobe or display to aid in illuminating the images to be captured. The above descriptions of the various embodiments of the invention will assume that such a display and image capture apparatus 500 may be employed. The invention, however, shall not be so limited and may be employed on any structure of image capture camera and display, whether contained in a single or multiple apparatuses, or any other appropriate system for capturing images and providing processing as described above. Furthermore, it is contemplated in accordance with the invention that image capture and processing may be implemented in a cloud computing environment, with an image capture device forwarding captured images to a remote location for storage and processing. Responses contemplated in accordance with the above description may be provided to the image capture device in manners known to those of ordinary skill in the art.

Therefore, in accordance with the invention, a method and apparatus are provided that allow for the automated confirmation of a user placing a pill in their mouth, for environments that have high or low computing power.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description and following claims are intended to cover all of the generic and specific features of the invention herein described and all statements of the scope of the invention which, as a matter of language, might be said to fall there between.

What is claimed is:

1. A display and image capture apparatus for monitoring medication adherence of a user, comprising:
    an image capture device for capturing one or more video sequences associated with administration of medication by the user;
    a computer processor associated with the image capture device arranged to receive the captured one or more video sequences, and to determine, based at least in part on the captured one or more video sequences, whether the user has properly performed a predetermined portion of a predetermined process representative of proper medication adherence by the user; and
    a presentation device, associated with the image capture device, arranged to present visually to the user one or more instructions encouraging proper performance of the predetermined portion of the predetermined process representative of proper medication adherence if the computer processor has determined that the user has not properly performed the predetermined portion of the predetermined process.

2. The apparatus of claim 1, wherein the computer processor is operable to determine whether the user has performed the predetermined portion of the predetermined process representative of proper medication adherence by determining at least one of: (i) that the user has properly positioned the user's face in a field of view of the image capture device, (ii) that the user has properly positioned a pill in the field of view of the image capture device, (iii) that the user has properly placed the pill in the user's mouth, (iv) that the user has properly drank a glass of liquid in the field of view of the image capture device, or (v) that the user has properly displayed the user's empty mouth in the field of view of the image capture device.

3. The apparatus of claim 2, wherein the computer processor is operable to determine that the user has properly placed the pill in the user's mouth by extracting one or more features associated with the pill, determining a confidence score for each of the one or more features representative of a likelihood that the pill captured in the one or more video sequences is a predetermined type of pill, and performing a decision fusion process on all of the determined confidence scores to determine whether the pill is a proper pill.

4. The apparatus of claim 2, wherein the computer processor is operable to determine, in accordance with a deep learning analysis system for extracting one or more features associated with the pill, that the user has properly placed the pill in the user's mouth and to determine whether the pill is a proper pill.

5. The apparatus of claim 2, wherein the computer processor is operable to determine that the user has properly placed the pill in the user's mouth by extracting one or more features associated with the pill, performing a feature fusion process on all of the one or more extracted features associated with the pill, and determining a score in accordance with the one or more extracted features to determine whether the pill is a proper pill.

6. The apparatus of claim 1, further comprising a communication system for transmitting one or more indications related to performance of the predetermined portion of the predetermined process to a remote location.

7. The apparatus of claim 6, comprising a computer processor at a remote location, wherein the computer processor at the remote location is operable to perform additional processing on the transmitted one or more indications related to performance of the predetermined portion of the predetermined process, and to transmit to the display and image capture apparatus one or more results of the additional processing.

8. The apparatus of claim 1, further comprising a communication system for transmitting the captured one or more video sequences to a remote location.

9. The apparatus of claim 8 arranged to transmit the captured one or more video sequences to the remote location over a series of administrations.

10. The apparatus of claim 9, comprising a computer processor at the remote location, wherein the computer processor at the remote location is operable to determine whether the user has properly administered the medication in accordance with the series of administrations.

11. The apparatus of claim 10, wherein the computer processor at the remote location is operable to extract one or more suspicious activity indicators in accordance with the series of administrations.

12. The apparatus of claim 11, wherein the apparatus is arranged to report the extracted one or more suspicious activity indicators to a third party.

13. The apparatus of claim 11, wherein the one or more suspicious activity indicators are selected from a group consisting of: hand movement, mouth movement, cheek shape, swallowing, audio sounds, face movement, and time on task.

14. The apparatus of claim 1, wherein the predetermined portion of the predetermined process comprises intake of medication into the user's body, and wherein the intake of the medication into the user's body includes ingestion of the medication orally by the user.

15. The apparatus of claim 1, wherein the presentation device is further arranged to present audibly to the user one or more instruction encouraging proper performance of the predetermined portion of the predetermined process representative of proper medication adherence in response to the computer processor's determining that the user has not properly performed the predetermined portion of the predetermined process, and arranged to present audibly an acknowledgment of proper performance of the predetermined portion of the predetermined process representative of proper medication adherence in response to the computer processor's determining that the user has properly performed the predetermined portion of the predetermined process.

* * * * *